US009302098B2

(12) United States Patent
Zhang et al.

(10) Patent No.: US 9,302,098 B2
(45) Date of Patent: Apr. 5, 2016

(54) IMPLANTABLE MEDICAL DEVICE INCLUDING ASSEMBLY INCORPORATING RADIOPAQUE AGENT AND ELUTABLE DRUG INTO A POLYMERIC LEAD TIP

(71) Applicant: Cardiac Pacemakers, Inc., St. Paul, MN (US)

(72) Inventors: Steve H. Zhang, Blaine, MN (US); Bryan Clem, Mound, MN (US); Daniel I. Codner, Isanti, MN (US); Arthur J. Foster, Blaine, MN (US); Peter J. Wolf, Dresser, WI (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 6 days.

(21) Appl. No.: 14/189,059

(22) Filed: Feb. 25, 2014

(65) Prior Publication Data
US 2014/0243946 A1    Aug. 28, 2014

Related U.S. Application Data

(60) Provisional application No. 61/769,555, filed on Feb. 26, 2013.

(51) Int. Cl.
*A61N 1/05* (2006.01)
(52) U.S. Cl.
CPC ............ *A61N 1/0568* (2013.01); *A61N 1/0573* (2013.01)
(58) Field of Classification Search
CPC ........................... A61N 1/0568; A61N 1/0573

USPC .......................................................... 607/120
See application file for complete search history.

(56) References Cited

U.S. PATENT DOCUMENTS

| 7,766,942 B2 | 8/2010 | Patterson et al. |
| 7,968,037 B2 | 6/2011 | Patterson et al. |
| 2008/0069856 A1* | 3/2008 | Lyu et al. ...................... 424/426 |
| 2008/0234532 A1 | 9/2008 | De Langen et al. |
| 2010/0305672 A1* | 12/2010 | Felling et al. ................. 607/116 |
| 2011/0052787 A1 | 3/2011 | Hum et al. |
| 2012/0292814 A1* | 11/2012 | Spratt et al. ................... 264/259 |

FOREIGN PATENT DOCUMENTS

| EP | 1857073 A1 | 11/2007 |
| WO | 2014133998 A1 | 9/2014 |

OTHER PUBLICATIONS

International Search Report and Written Opinion issued in PCT/US2014/018195, mailed Jun. 12, 2014, 12 pgs.
International Search Report and Written Opinion issued in PCT/US2014/018195, mailed Sep. 11, 2015, 9 pages.

* cited by examiner

*Primary Examiner* — Carl H Layno
*Assistant Examiner* — Erin M Piateski
(74) *Attorney, Agent, or Firm* — Faegre Baker Daniels LLP

(57) ABSTRACT

An assembly for an implantable device can be made from PEEK and can incorporate one or more radiopaque agents and one or more elutable drug components into a polymeric lead tip. The assembly can be machined or injection molded and can be configured, for example, as a housing for an active fixation lead or as an electrode base supporting a foil electrode.

8 Claims, 6 Drawing Sheets

IMPLANTABLE MEDICAL DEVICE INCLUDING ASSEMBLY INCORPORATING RADIOPAQUE AGENT AND ELUTABLE DRUG INTO A POLYMERIC LEAD TIP

CROSS-REFERENCE TO RELATED APPLICATIONS

This application claims the benefit under 35 U.S.C. §119 (e) to U.S. Provisional Application 61/769,555, filed on Feb. 26, 2013, which is herein incorporated by reference in its entirety.

TECHNICAL FIELD

The present invention relates to implantable medical devices and relates more particularly to leads for cardiac rhythm management (CRM) systems.

BACKGROUND

Various types of medical electrical leads for use in CRM and neurostimulation systems are known. For CRM systems, such leads are typically extended intravascularly to an implantation location within or on a patient's heart, and thereafter coupled to a pulse generator or other implantable device for sensing cardiac electrical activity, delivering therapeutic stimuli, and the like. The leads frequently include features to facilitate securing the lead to heart tissue to maintain the lead at its desired implantation site.

SUMMARY

Example 1 is an implantable lead having a flexible body, a connector assembly secured to a proximal end of the flexible body for coupling to an implantable medical device and a distal assembly coupled to a distal end of the flexible body. The connector assembly includes a terminal pin that is rotatable relative to the body. A conductor member is disposed longitudinally within the body and is rotatable relative to the body, and is coupled to the terminal pin. The distal assembly includes a housing having a proximal region that is fixedly coupled the distal end of the body. The housing is formed from a polymeric material. A radiopaque agent is dispersed within the polymeric material. An elutable drug component is dispersed within the polymeric material. A coupler having a proximal end is connected at its proximal end to the conductor member, the coupler being rotatably disposed within the housing. A helical electrode is fixedly secured to the coupler. The terminal pin is rotatably engaged with the coupler via the conductor member such that rotation of the terminal pin causes the coupler and the helical electrode to rotate and therefore translate relative to the housing.

Example 2 includes Example 1 and specifies that the polymeric material includes polyetheretherketone.

Example 3 includes Examples 1 and 2 and specifies that the housing includes an at least substantially homogenous mixture of radiopaque agent, elutable drug component and polyetheretherketone.

Example 4 includes Examples 1 through 3 and specifies that the polymeric material forming the housing includes about 5 to about 80 weight percent radiopaque agent, about 1 to about 50 weight percent elutable drug component and a balance polyetheretherketone.

Example 5 includes Examples 1 through 4 and specifies that the polymeric material forming the housing includes about 30 to about 70 weight percent radiopaque agent, about 10 to about 35 weight percent elutable drug component and a balance polyetheretherketone.

Example 6 includes Examples 1 through 5 and specifies that the polymeric material forming the housing includes about 40 to about 60 weight percent radiopaque agent, about 15 to about 25 weight percent elutable drug component and a balance polyetheretherketone.

Example 7 includes Examples 1 through 6 and specifies that the radiopaque agent includes one or more of barium sulfate, barium trioxide, tungsten, platinum, iridium and alloys thereof.

Example 8 includes Examples 1 through 7 and specifies that the elutable drug component includes a steroid.

Example 9 is an implantable lead that is configured to carry an electrical signal. The implantable lead includes a flexible body extending between a proximal portion and a distal portion, the body configured to carry an electrical signal from the proximal portion to the distal portion. An assembly is coupled to the distal portion of the flexible body, the assembly formed from an at least substantially homogenous combination of polyetheretherketone, radiopaque agent and elutable drug component.

Example 10 includes Example 9 and specifies that the assembly includes a housing extending from the distal portion of the flexible body, the implantable lead further including a coupler that is disposed within the housing and a fixation helix that is secured to the coupler.

Example 11 includes Example 9 and specifies that the implantable lead further includes a foil electrode, and the assembly is an electrode base that is configured to support the foil electrode.

Example 12 includes Example 11 and specifies that the electrode base has an outer surface having a first region and a second region, the first region supporting the foil electrode and the second region uncovered to permit drug elution from the electrode base.

Example 13 includes Examples 9 through 12 and specifies that the assembly includes about 5 to about 80 weight percent radiopaque agent, about 1 to about 50 weight percent elutable drug component and a balance polyetheretherketone.

Example 14 includes Examples 9 through 13 and specifies that the assembly includes about 30 to about 70 weight percent radiopaque agent, about 10 to about 35 weight percent elutable drug component and a balance polyetheretherketone.

Example 15 includes Examples 9 through 14 and specifies that the assembly includes about 40 to about 60 weight percent radiopaque agent, about 15 to about 25 weight percent elutable drug component and a balance polyetheretherketone.

Example 16 includes Examples 9 through 15 and specifies that the radiopaque agent includes one or more of barium sulfate, barium trioxide, tungsten, platinum, iridium and alloys thereof.

Example 17 includes Examples 9 through 16 and specifies that the elutable drug component includes one or more of dexamethasone, betamethasone, paramethasone, beclomethasone, clobetasol, triamcinolone, prednisone, prednisolone and derivatives thereof.

Example 18 is an implantable lead that is configured to carry an electrical signal. The lead includes a flexible body extending between a proximal portion and a distal portion, the body configured to carry an electrical signal from the proximal portion to the distal portion. An electrode base is coupled to the distal portion of the flexible body and a foil electrode is supported by a portion of the electrode base. The electrode base is formed from an at least substantially homogenous combination of polyetheretherketone, radiopaque agent and elutable drug component.

Example 19 includes Example 18 and specifies that the electrode base has an outer surface having a first region and a second region, the first region having a first diameter and supporting the foil electrode and the second region having a second diameter greater than the first diameter, the second region uncovered to permit drug elution from the electrode base.

Example 20 includes Examples 18 and 19 and specifies that the electrode base includes about 5 to about 80 weight percent radiopaque agent, about 1 to about 50 weight percent elutable drug component and a balance polyetheretherketone.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
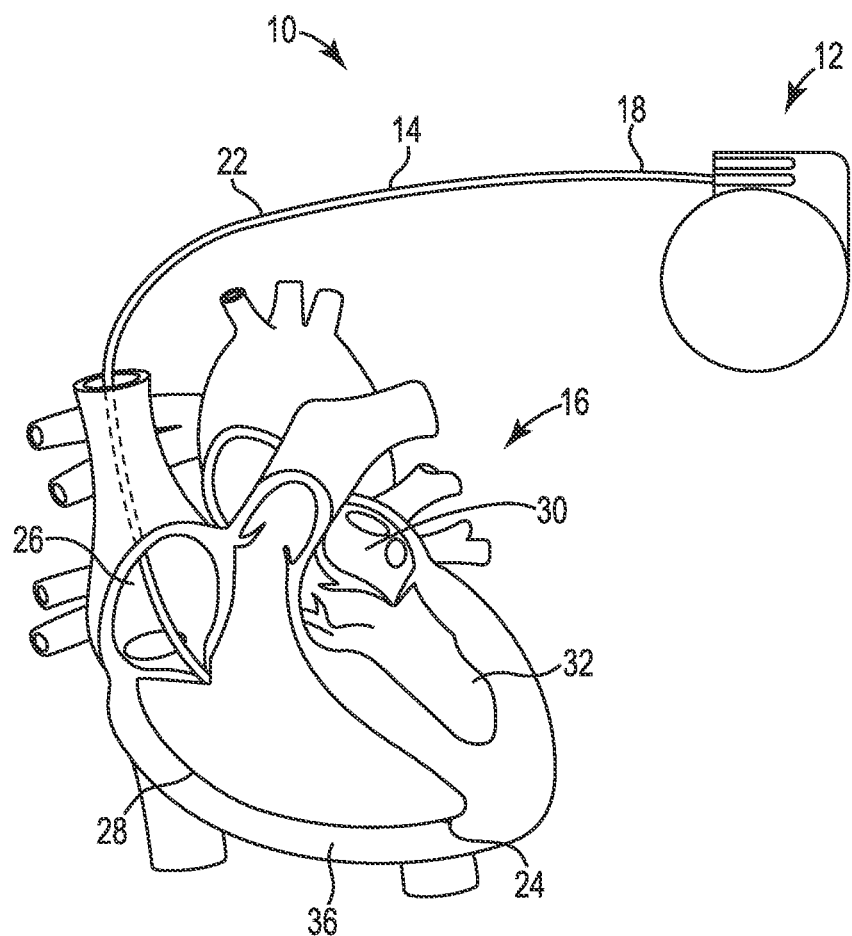
FIG. 1 is a combined cutaway and perspective view of an implantable medical device and lead in accordance with an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents and alternatives falling within the scope of the invention as defined by the appended claims.

DETAILED DESCRIPTION

FIG. 1 is a perspective view of an implantable CRM system 10. The CRM system 10 includes a pulse generator 12 and a cardiac lead 14. The lead 14 operates to convey electrical signals between the heart 16 and the pulse generator 12. The lead 14 has a proximal region 18 and a distal region 20. The lead 14 includes a lead body 22 extending from the proximal region 18 to the distal region 20. The proximal region 18 is coupled to the pulse generator 12 and the distal region 20 is coupled to the heart 16. The distal region 20 includes an extendable/retractable fixation helix 24, which locates and/or secures the distal region 20 within the heart 16.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardioverter/defibrillator (ICD), a cardiac resynchronization therapy (CRT) device configured for bi-ventricular pacing, and/or includes combinations of pacing, CRT, and defibrillation capabilities.

The lead body 22 can be made from any flexible, biocompatible materials suitable for lead construction. In various embodiments, the lead body 22 is made from a flexible, electrically insulative material. In one embodiment, the lead body 22 is made from silicone rubber. In another embodiment, the lead body 22 is made from polyurethane. In various embodiments, respective segments of the lead body 22 are made from different materials, so as to tailor the lead body characteristics to its intended clinical and operating environments. In various embodiments, the proximal and distal ends of the lead body 22 are made from different materials selected to provide desired functionalities.

As is known in the art, the heart 16 includes a right atrium 26, a right ventricle 28, a left atrium 30 and a left ventricle 32. It can be seen that the heart 16 includes an endothelial inner lining or endocardium 34 covering the myocardium 36. In some embodiments, as illustrated, the fixation helix 24, located at the distal region 20 of the lead, penetrates through the endocardium 34 and is imbedded within the myocardium 36. In one embodiment, the CRM system 10 includes a plurality of leads 14. For example, it can include a first lead 14 adapted to convey electrical signals between the pulse generator 12 and the right ventricle 28 and a second lead (not shown) adapted to convey electrical signals between the pulse generator 12 and the right atrium 26.

In the illustrated embodiment shown in FIG. 1, the fixation helix 24 penetrates the endocardium 34 of the right ventricle 28 and is embedded in the myocardium 36 of the heart 16. In some embodiments, the fixation helix 24 is electrically active and thus can be used to sense the electrical activity of the heart 16 and/or to apply a stimulating pulse to the right ventricle 28. In other embodiments, the fixation helix 24 is not electrically active. Rather, in some embodiments, other components of the lead 14 are electrically active.

Figure 2:
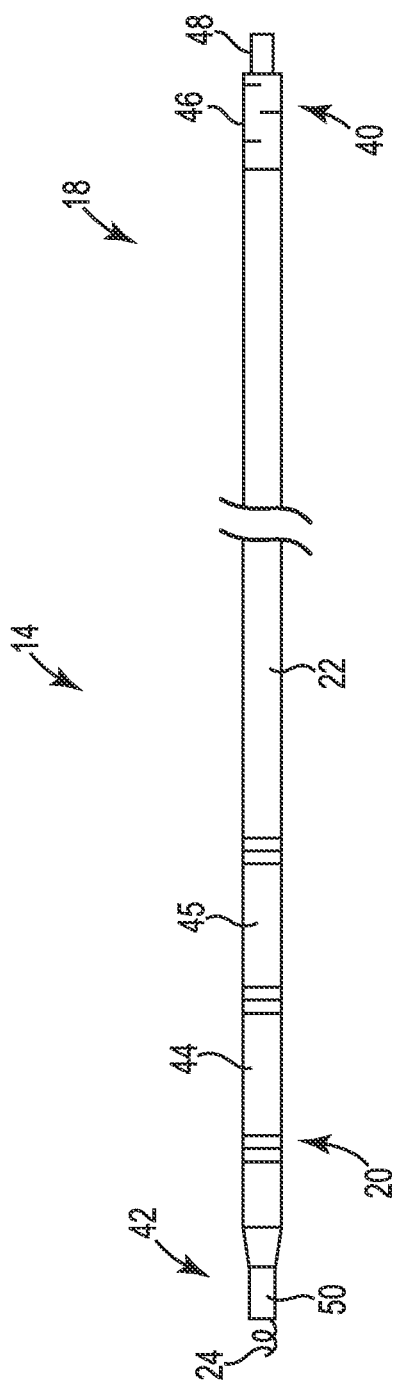
FIG. 2 is a side elevation view of the lead of FIG. 1.

FIG. 2 is an isometric illustration of the lead 14. A connector assembly 40 is disposed at or near the proximal region 18 of the lead 14 while a distal assembly 42 is disposed at or near the distal region 20 of the lead 14. Depending on the functional requirements of the CRM system 10 (see FIG. 1) and the therapeutic needs of a patient, the distal region 20 can include one or more electrodes. In the illustrated embodiment, the distal region 20 includes a pair of coil electrodes 44 and 45 that can function as shocking electrodes for providing a defibrillation shock to the heart 16.

In various embodiments, the lead 14 can include only a single coil electrode. In various other embodiments, the lead 14 includes one or more ring electrodes (not shown) along the lead body 22 in lieu of or in addition to the coil electrodes 44, 45. When present, the ring electrodes operate as relatively low voltage pace/sense electrodes. In short, a wide range of electrode combinations can be incorporated into the lead 14 within the scope of the various embodiments of the present invention.

The connector assembly 40 includes a connector 46 and a terminal pin 48. The connector 46 is configured to be coupled to the lead body 22 and is configured to mechanically and electrically couple the lead 14 to a header on the pulse generator 12 (see FIG. 1). In various embodiments, the terminal pin 48 extends proximally from the connector 46 and in some embodiments is coupled to a conductor member (not visible in this view) that extends longitudinally within the lead body 22 and which is rotatable relative to the lead body 22 such that rotating the terminal pin 48 (relative to the lead body 22) causes the conductor member to rotate within the lead body 22 as well. In some embodiments, the terminal pin 48 includes an aperture extending therethrough, and the conductor member defines a longitudinal lumen in communication with the aperture. When present, the aperture and/or conductor lumen are configured to accommodate a guide wire or an insertion stylet for delivery of the lead 14.

In some embodiments, the distal assembly 42 includes a housing 50, within which the fixation helix 24 is at least partially disposed. In some embodiments, the housing 50 includes or accommodates a mechanism that enables the fixation helix 24 to move distally and proximally relative to the housing 50. In some embodiments, the housing 50 can accommodate or include structure that limits distal travel of the fixation helix 24 (relative to the housing 50). As noted above, the fixation helix 24 operates as an anchoring means for anchoring the distal region 20 of the lead 14 within the heart 16. In some embodiments, the fixation helix 24 is electrically active, and is also used as a pace/sense electrode. In some embodiments, the fixation helix 24 is made of an electrically conductive material such as Elgiloy, MP35N, tungsten, tantalum, iridium, platinum, titanium, palladium, or stainless steel, as well as alloys of any of these materials. In some embodiments, the fixation helix 24 is made of a non-electrically conductive material which includes polymeric materials such as polyetheretherketone (PEEK), polyethersulfone (PES), polyimide (PI), polyamide (PA), liquid crystal polymer (LCP), polyethylene terephthalate (PET), polybutylene terephthalate (PBT), polyurethane (PU), polypropylene (PP) and any combinations of these polymers, and ceramics.

Figure 3:
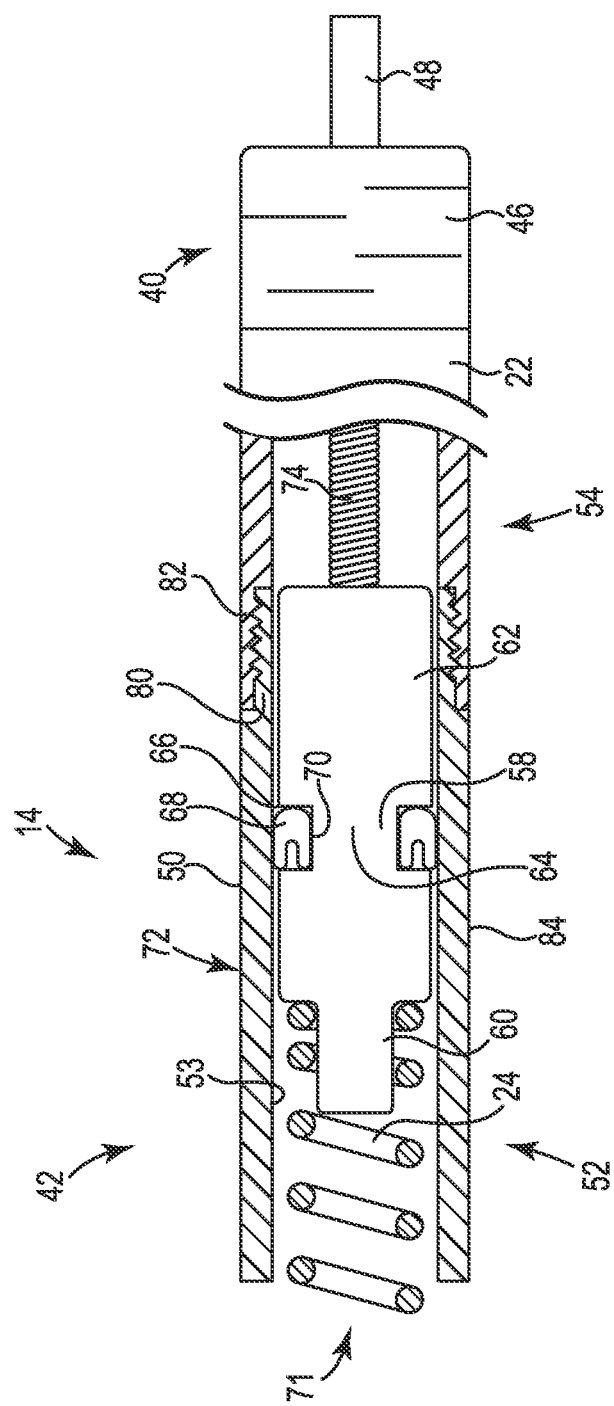
FIG. 3 is a partial cross-sectional view of the lead of FIG. 1.

FIG. 3 illustrates an embodiment of a lead including distal assemblies in accordance with the present invention. FIG. 3 is a partial cross-section of the lead 14 that include the distal assembly 42. In the illustrated embodiment, the fixation helix 24 is electrically active so as to be operable as a pace/sense electrode.

As shown in FIG. 3, the housing 50 includes a distal region 52 and a proximal region 54. The housing 50 has an inner surface 53. The housing 50 is, in general, relatively rigid or semi-rigid. In some embodiments, the housing 50 can be formed via injection molding. In other embodiments, the housing 50 can be formed via a machining process. In some embodiments, the housing 50 can include a threaded portion 80 that interacts with a cooperating threaded portion 82 formed in an end of the lead body 22. In some embodiments, the housing 50 can have an outer surface 84 having a largely uniform cross-sectional diameter by virtue of not having to incorporate separate fluoro rings and/or drug collars, as will be discussed in greater detail.

In some embodiments, the housing 50 is made of a non-electrically conductive material which includes polymeric material such as polyetheretherketone (PEEK), polyethersulfone (PES), polyimide (PI), polyamide (PA), liquid crystal polymer (LCP), polyethylene terephthalate (PET), polybutylene terephthalate (PBT), polyurethane (PU), and polypropylene (PP) and any combinations of these polymers as well as ceramics. In some embodiments, the housing 50 is cast or molded from polyetheretherketone (PEEK) that incorporates one or more radiopaque agents as well as one or more elutable drug components.

One or more radiopaque agents can be dispersed within the polymeric material in order to provide the housing 50 with a desired level of visibility when viewed using fluoroscopic techniques during and after implantation without requiring a separate fluoro ring. One or more elutable drug components may be dispersed within the polymeric material in order to provide a time-released dosage of a steroid or another anti-inflammatory agent to the tissue to be stimulated, e.g., the heart tissue in which the electrically active fixation helix 24 is implanted without requiring a separate drug collar.

In some embodiments, the housing 50 can be formed from an at least substantially homogenous mixture of the radiopaque agent, the elutable drug component and the polymeric material. In some embodiments, the polymeric material is PEEK. As used herein, "substantially homogenous" may be defined as the composition of the bulk mixture, or the composition of an article formed from the mixture, varying by less than about ten percent, regardless of where in the mixture (or the article) the composition is sampled.

In some embodiments, the housing 50 can be formed from a polymeric mixture that includes about 1 to about 80 weight percent of a radiopaque agent and about 15 to about 50 weight percent of an elutable drug component, with the balance being the polymeric material. It will be appreciated that in these compositional ranges, relatively small amounts of additives such as fillers, antioxidants, colorants, conductive agents and processing aids may be included, and can be part of the polymeric material portion of the composition.

In some embodiments, the housing 50 can be formed from a polymeric mixture that includes about 30 to about 70 weight percent of a radiopaque agent and about 10 to about 35 weight percent of an elutable drug component, with the balance being PEEK. In some embodiments, the housing 50 can be formed from a polymeric mixture that includes about 40 to about 60 weight percent of a radiopaque agent and about 15 to about 25 weight percent of an elutable drug component, with the balance being the polymeric material.

A variety of different radiopaque agents can be used. Illustrative but non-limiting examples of suitable radiopaque agents include barium sulfate, barium trioxide, tungsten, platinum, iridium, and alloys thereof. In some embodiments, a single radiopaque agent can be used. In some embodiments, combinations of two or more distinct radiopaque agents can be combined into the polymeric material.

A variety of different elutable drug components can be used. In this, an elutable drug component is a drug or drug precursor that is able to diffuse through and thus elute from the surface of the polymeric material. In some embodiments, the elutable drug component can be a steroid. Illustrative but non-limiting examples of suitable steroids include dexamethasone, betamethasone, paramethasone, beclomethasone, clobetasol, triamcinolone, prednisone, prednisolone, and derivatives thereof. In some embodiments, a single steroid can be used. In some embodiments, combinations of two or more distinct steroids can be combined into the polymeric material.

As shown, the distal assembly 42 includes a coupler 58. In some embodiments, the coupler 58 is formed of a metallic material and is configured to move longitudinally and/or rotationally with respect to the housing 50. The coupler 58 includes a distal portion 60, a proximal portion 62 and a central portion 64. As shown, the fixation helix 24 is connected to the distal portion 60 of the coupler 58. In some embodiments, as illustrated, the distal portion 60 may have a relatively smaller diameter (relative to at least part of the central portion 64) that is configured to accommodate the fixation helix 24.

In some embodiments, as illustrated, the central portion 64 of the coupler 58 includes a sealing groove 66 that is configured to accommodate an annular seal 68. The sealing groove 66 has a bottom surface 70 that provides a surface for the annular seal 68 to seat against. The annular seal 68 is configured to provide a substantially fluid-tight seal between the coupler 58 and the inner surface 53 of the housing 50 while minimizing frictional forces caused by the annular seal 68. In some embodiments, the lead 14 can include one or more other seals, and thus may not include the annular seal 68 or the sealing groove 66.

The fixation helix 24 has a distal region 71 and a proximal region 72. The proximal region 72 is secured to the distal portion 60 of the coupler 58. One or more attachment methods are used to secure the fixation helix 24 to the coupler 58. In some embodiments, the proximal region 72 of the fixation helix 24 is welded or soldered onto the distal portion 60 of the coupler 58. In some embodiments, the proximal region 72 of the fixation helix 24 has an inner diameter that is less than an outer diameter of the distal portion 60 of the coupler 58, and thus is held in place via compressive forces. In some embodiments, multiple attachment methods are used.

A conductor member 74 is secured to the proximal portion 62 of the coupler 58, and extends proximally through the lead body 22 to the connector assembly 40. In some embodiments, the conductor member 74 includes or is otherwise formed from a metallic coil. The coupler 58 provides an electrical connection between the conductor member 74 and the fixation helix 24. In the connector assembly 40, the conductor member 74 is coupled to the terminal pin 48 such that rotation of the terminal pin 48 causes the conductor member 74 to rotate. As the conductor member 74 rotates, the coupler 58 and the fixation helix 24 will also rotate. In some embodiments, the fixation helix 24 is rotated via a stylet that is inserted through an aperture that may be formed within the terminal pin 48 (FIG. 2). The distal assembly 42 is configured so that relative rotation of the coupler 58 and fixation helix 24 relative to the housing 50 results in longitudinal translation of the coupler 58 and fixation helix 24 relative to the housing 50, thereby providing the extendable/retractable functionality of the fixation helix 24.

The particular arrangement illustrated for facilitating extension and retraction of the fixation helix 24 is exemplary only. In other words, any arrangement, whether now known or later developed, for providing the extendable/retractable functionality of the fixation helix 24 can be utilized in connection with the various embodiments of the present invention. In one embodiment, the lead 14 includes structures such as those described and illustrated in co-pending and commonly assigned U.S. Patent Publication 2010/0305672, the disclosure of which is incorporated by reference herein in its entirety. In other embodiments, a different arrangement for extending and retracting the fixation helix 24 is utilized.

The preceding Figures illustrate an active fixation lead 14 that includes a housing 50. In some embodiments, both active and fixation leads may include an assembly that is from a combination of radiopaque agent, elutable drug component and polymeric material. In some embodiments, as shown above, the assembly may be a housing that is secured to a lead and that accommodates a coupler and active fixation helix therein. In some embodiments, as described with respect to FIGS. 4 through 6, the aforementioned assembly can instead include a foil electrode and an electrode base that is configured to support the foil electrode.

Figure 4:
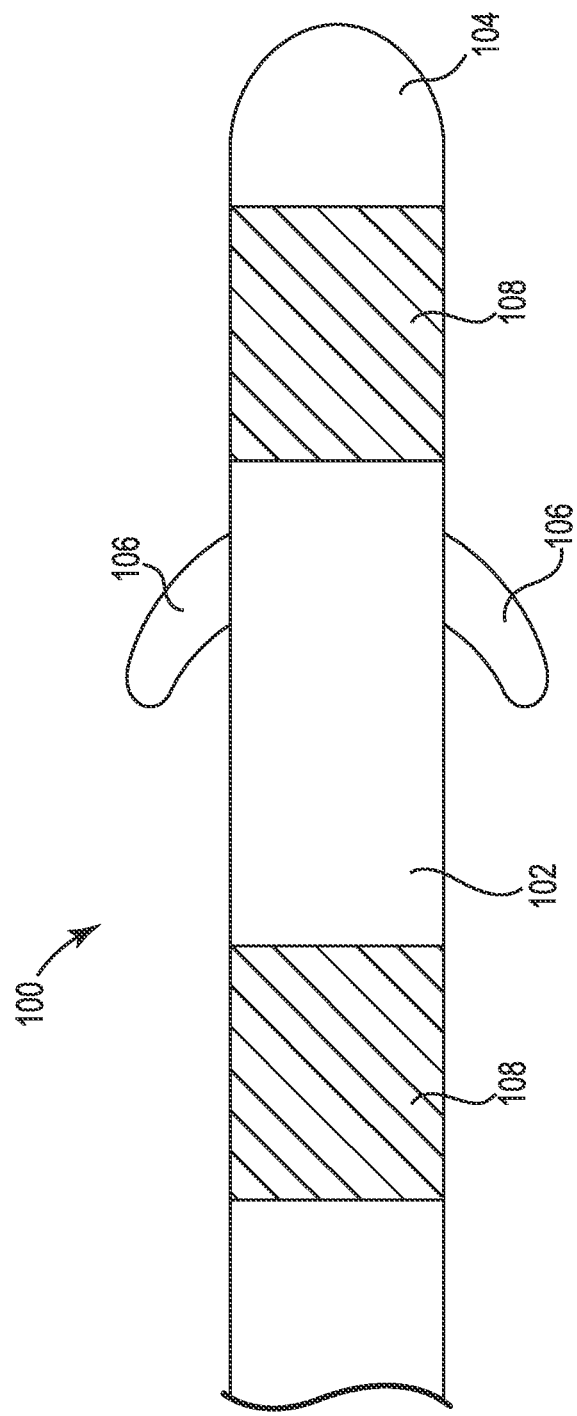
FIG. 4 is a side elevation view of a portion of a passive fixation lead in accordance with an embodiment of the present invention.

FIG. 4 is a side elevation view of a distal portion of a passive fixation lead 100. The lead 100 includes a lead body 102 and a distal tip 104. One or more passive fixation wings 106 extend from the lead body 102 and can be used to help secure the lead 100 within the desired vasculature or location of the heart. In some embodiments, the lead body 102, the distal tip 104, and the passive fixation wings 106 can be formed from any flexible, biocompatible materials suitable for lead construction, including flexible, electrically insulative materials.

In one embodiment, the lead body 102, distal tip 104 and/or passive fixation wings 106 are made from silicone rubber or polyurethane. In various embodiments, respective segments of the lead 100 are made from different materials, so as to tailor the lead body characteristics to its intended clinical and operating environments. In various embodiments, the proximal and distal ends of the lead 100 are made from different materials selected to provide desired functionalities.

As illustrated, the lead 100 also includes several electrodes 108. While two electrodes are illustrated, in some embodiments the lead 100 can include a single electrode 108. In other embodiments, the lead 100 can include three or more electrodes 108. The construction of the electrode 108 is illustrated with respect to FIGS. 5 and 6, which illustrate the electrode 108 as including an electrode base and a foil electrode supported by the electrode base.

Figure 5:
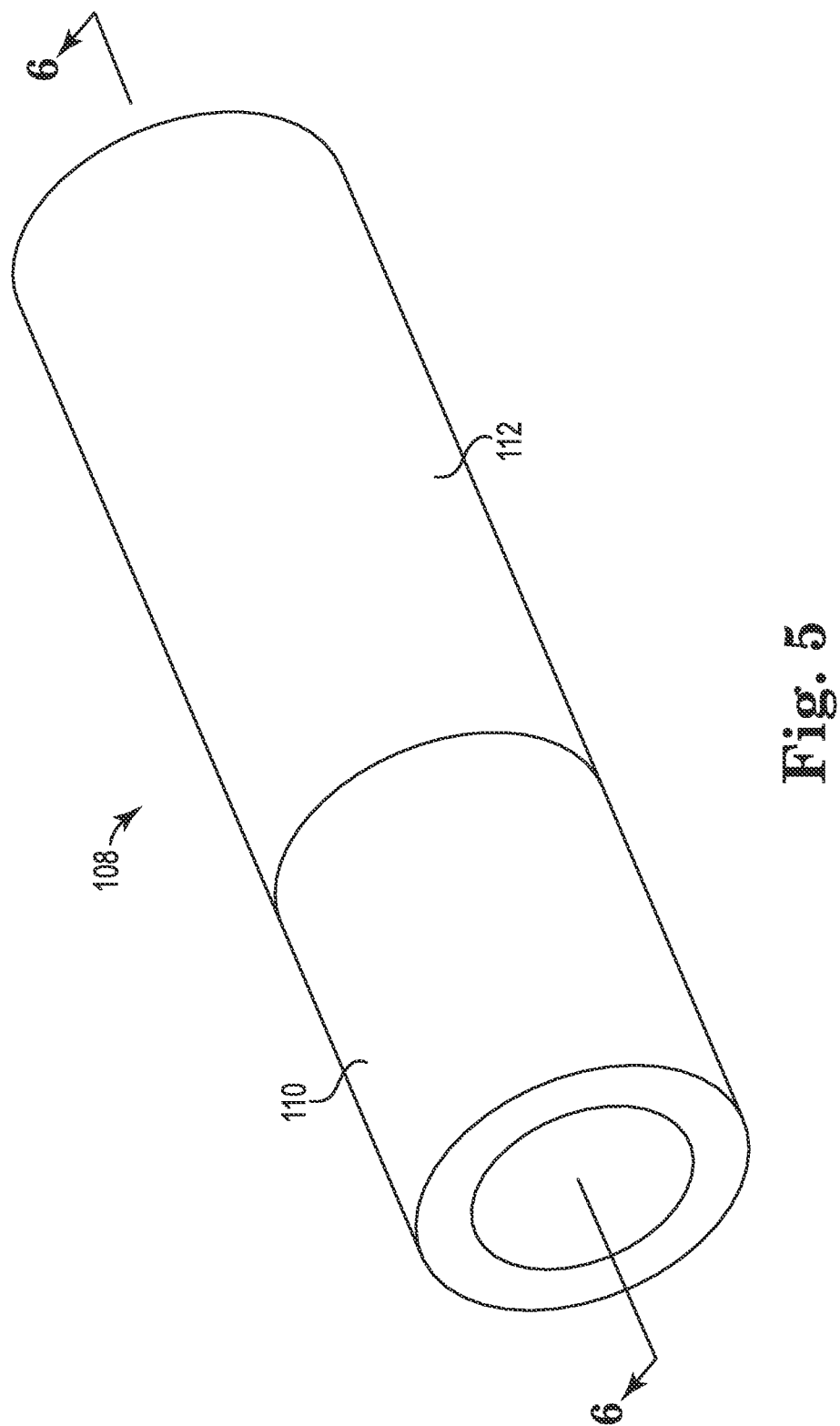
FIG. 5 is a perspective view of an electrode base and electrode useful in the passive fixation lead of FIG. 4 in accordance with an embodiment of the present invention.
Figure 6:
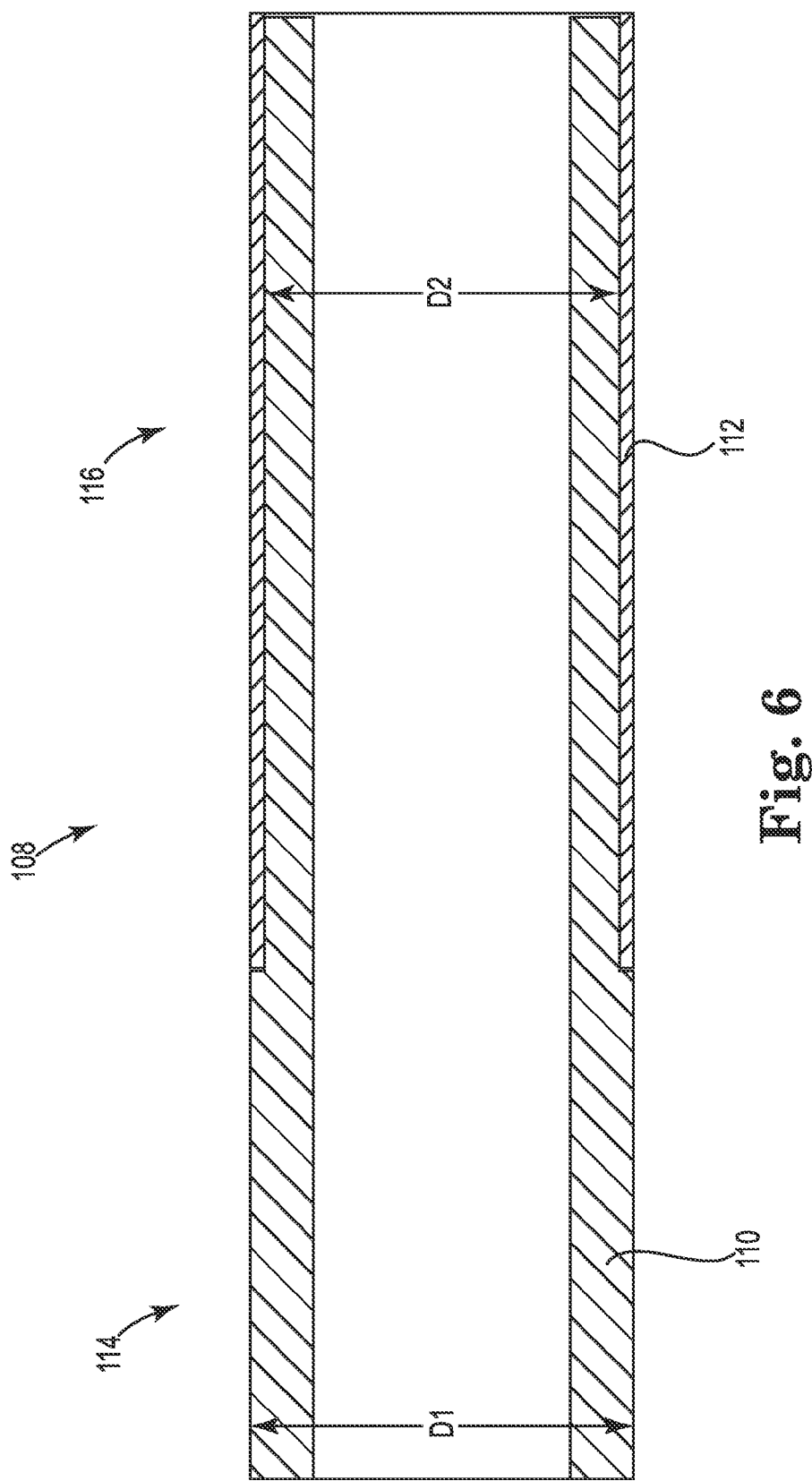
FIG. 6 is a cross-sectional view of the electrode base and electrode of FIG. 5.

FIG. 5 is a perspective view of one of the electrodes 108 and FIG. 6 is a cross-sectional view taken along line 6-6 of FIG. 5. As illustrated, the electrode 108 includes an electrode base 110 and a foil electrode 112. It will be appreciated that by including the electrode base 110 to support the foil electrode 112, a substantially thinner electrode can be used. In some embodiments, the electrode base 108 can be considered as including a first region 114 having a first diameter D1 and a second region 116 having a second diameter D2 that is less than the first diameter D1. In some embodiments, as illustrated, the difference between D1 and D2 represents a thickness of the foil electrode 112. In some embodiments, the foil electrode 112 can include structure (not illustrated) that permits the foil electrode 112 to be electrically coupled to a conductor extending through the lead 100.

As discussed above with respect to the housing 50, the electrode base 110 can, in some embodiments, be formed from an at least substantially homogenous mixture of radiopaque agent, elutable drug component and PEEK. The specific radiopaque agents that can be used in forming the electrode base 110 are the same as those discussed with respect to the housing 50. The specific elutable drug components are the same as those discussed with respect to the housing 50.

In some embodiments, the electrode base 110 can be formed from a polymeric mixture that includes about 20 to about 80 weight percent of a radiopaque agent and about 5 to about 40 weight percent of an elutable drug component, with the balance being a polymeric material such as PEEK. It will be appreciated that in these compositional ranges, relatively small amounts of additives such as fillers, antioxidants, colorants, conductive agents and processing aids may be included and can be part of the polymeric material portion of the composition.

In some embodiments, the electrode base 110 can be formed from a polymeric mixture that includes about 30 to about 70 weight percent of a radiopaque agent and about 10 to about 35 weight percent of an elutable drug component, with the balance being a polymeric material such as PEEK. In some embodiments, the electrode base 110 can be formed from a polymeric mixture that includes about 40 to about 60 weight percent of a radiopaque agent and about 15 to about 25 weight percent of an elutable drug component, with the balance being a polymeric material such as PEEK.

The foil electrode 112 can be made of any suitable conductive material such as, but not limited to, MP35N, tungsten, tantalum, iridium, platinum, titanium, palladium, stainless steel, as well as alloys of any of these materials. As noted, the foil electrode 112 can be relatively thin, with a thickness about equal to the difference between D1 and D2. In some embodiments, the foil electrode 112 can have a thickness that is in the range of about 0.0001 inches to about 0.005 inches.

In some embodiments, the foil electrode 112 can have a thickness of about 0.001 inches.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable lead comprising:
   a flexible body extending between a proximal end and a distal end;
   a connector assembly secured to the proximal end for coupling the lead to an implantable medical device, the connector assembly including a terminal pin rotatable relative to the body;
   a conductor member disposed longitudinally within the body and coupled to the terminal pin, the conductor member rotatable relative to the body; and
   a distal assembly coupled to the distal end of the body and including:
      a housing having a distal region and a proximal region, the proximal region fixedly coupled to the distal end of the body, the housing formed from a polymeric material;
      a radiopaque agent substantially homogeneously dispersed within the polymeric material forming the housing;
      an elutable drug component substantially homogeneously dispersed within the polymeric material forming the housing;
      a coupler rotatably disposed within the housing, the coupler having a proximal end and a distal end, the proximal end connected to the conductor member; and
      a helical electrode fixedly secured to the coupler;
   wherein the terminal pin is rotatably engaged with the coupler via the conductor member such that rotation of the terminal pin causes the coupler and the helical electrode to rotate and therefore translate relative to the housing.

2. The implantable lead of claim 1, wherein the polymeric material comprises polyetheretherketone.

3. The implantable lead of claim 1, wherein the housing comprises an at least substantially homogenous mixture of radiopaque agent, elutable drug component and polyetheretherketone.

4. The implantable lead of claim 1, wherein the polymeric material forming the housing comprises:
   about 5 to about 80 weight percent of the radiopaque agent;
   about 1 to about 50 weight percent of the elutable drug component; and
   a balance polyetheretherketone.

5. The implantable lead of claim 1, wherein the polymeric material forming the housing comprises:
   about 30 to about 70 weight percent of the radiopaque agent;
   about 10 to about 35 weight percent of the elutable drug component; and
   a balance polyetheretherketone.

6. The implantable lead of claim 1, wherein the polymeric material forming the housing comprises:
   about 40 to about 60 weight percent of the radiopaque agent;
   about 15 to about 25 weight percent of the elutable drug component; and
   a balance polyetheretherketone.

7. The implantable lead of claim 1, wherein the radiopaque agent comprises one or more of barium sulfate, barium trioxide, tungsten, platinum, iridium and alloys thereof.

8. The implantable lead of claim 1, wherein the elutable drug component comprises a steroid.

* * * * *